United States Patent
Arbel et al.

(10) Patent No.: US 11,612,341 B2
(45) Date of Patent: Mar. 28, 2023

(54) SYSTEMS AND METHODS FOR ASSESSMENT AND MEASUREMENT OF REACTION TIME IN VIRTUAL/AUGMENTED REALITY

(71) Applicant: XR Health IL LTD, Tel Aviv (IL)

(72) Inventors: Tal Arbel, Hod-Hasharon (IL); Gili Karni, Nordia (IL); Omer Weissberger, Even-Yehuda (IL)

(73) Assignee: XR Health IL LTD, Tel Aviv (IL)

( * ) Notice: Subject to any disclaimer, the term of this patent is extended or adjusted under 35 U.S.C. 154(b) by 186 days.

(21) Appl. No.: 16/664,412

(22) Filed: Oct. 25, 2019

(65) Prior Publication Data
US 2020/0129106 A1    Apr. 30, 2020

Related U.S. Application Data

(60) Provisional application No. 62/750,671, filed on Oct. 25, 2018.

(51) Int. Cl.
| | |
|---|---|
| *A61B 5/16* | (2006.01) |
| *G06T 19/00* | (2011.01) |
| *G06F 3/04815* | (2022.01) |
| *G06F 3/01* | (2006.01) |
| *G02B 27/01* | (2006.01) |
| *G06F 3/048* | (2013.01) |

(52) U.S. Cl.
CPC ............ *A61B 5/162* (2013.01); *G02B 27/017* (2013.01); *G06F 3/011* (2013.01); *G06F 3/017* (2013.01); *G06F 3/04815* (2013.01); *G06T 19/006* (2013.01)

(58) Field of Classification Search
CPC ........ G06F 3/0482; G06F 3/011; G06F 3/017; G06F 3/04815; A61B 5/162; G02B 27/017; G06T 19/006
See application file for complete search history.

(56) References Cited

U.S. PATENT DOCUMENTS

| | | | |
|---|---|---|---|
| 10,529,137 B1 * | 1/2020 | Black ................... | G06V 40/103 |
| 2002/0183961 A1 | 12/2002 | French et al. | |
| 2004/0225955 A1 * | 11/2004 | Ly .......................... | G06Q 10/06 |
| | | | 715/255 |

(Continued)

OTHER PUBLICATIONS

International Search Report and Written Opinion for International Application No. PCT/IB2019/001159 dated Mar. 20, 2020.

*Primary Examiner* — Nicholas Augustine
(74) *Attorney, Agent, or Firm* — Erik A. Huestis; Foley Hoag LLP

(57) ABSTRACT

A virtual or augmented reality based system for assessment and measurement of reaction time is disclosed. In various embodiments the system, methods, and computer program products relate to assessing and measuring a reaction time of a patient/user in virtual reality (VR) or augmented reality (AR) environments. The VR/AR system may provide a sensory stimulus to the patient/user in the VR/AR environment, determine a plurality of motion parameters, and determine a reaction time based on the plurality of motion parameters by applying a time window selection model. In various embodiments, a time window shrinkage model may be applied after the time window selection model.

48 Claims, 11 Drawing Sheets

(56) References Cited

U.S. PATENT DOCUMENTS

| | | | |
|---|---|---|---|
| 2014/0214335 A1 | 7/2014 | Siefert | |
| 2014/0358475 A1* | 12/2014 | Boulkenafed | G06F 3/017 |
| | | | 702/152 |
| 2016/0170998 A1* | 6/2016 | Frank | G06F 16/9535 |
| | | | 707/748 |
| 2017/0004260 A1* | 1/2017 | Moturu | G16H 10/60 |
| 2017/0300933 A1* | 10/2017 | Mascaro | G06Q 10/0639 |
| 2018/0077538 A1* | 3/2018 | Matus | G08B 25/016 |
| 2018/0336481 A1* | 11/2018 | Guttmann | G06N 7/005 |
| 2019/0121431 A1* | 4/2019 | Lee | G06F 3/011 |
| 2020/0050884 A1* | 2/2020 | Han | H04N 13/117 |

* cited by examiner

SYSTEMS AND METHODS FOR ASSESSMENT AND MEASUREMENT OF REACTION TIME IN VIRTUAL/AUGMENTED REALITY

CROSS-REFERENCE TO RELATED APPLICATION

This application claims the benefit of U.S. Provisional Patent Application No. 62/750,671, filed on Oct. 25, 2018, which is hereby incorporated by reference in its entirety.

BACKGROUND

Embodiments of the present disclosure generally relate to assessment and measurement of reaction time in virtual reality (VR) or augmented reality (AR) environments.

BRIEF SUMMARY

Systems, methods, and computer program products of the present invention for assessment and measurement of reaction time are disclosed. In various embodiments, the method include providing a virtual environment to a user via a virtual or augmented reality system. The method further includes presenting a sensory stimulus to the user within the virtual environment. The method further includes determining a plurality of motion parameters corresponding to a user reaction to the stimulus. The method further includes determining a user reaction time from the plurality of motion parameters by applying a time window selection model.

In various embodiments, a computer program product includes a computer readable storage medium having program instructions embodied therewith. The program instructions are executable by a processor to cause the processor to perform a method including providing a virtual environment to a user via a virtual or augmented reality system. The method further includes presenting a sensory stimulus to the user within the virtual environment. The method further includes determining a plurality of motion parameters corresponding to a user reaction to the stimulus. The method further includes determining a user reaction time from the plurality of motion parameters by applying a time window selection model.

In various embodiments, a system includes a virtual or augmented reality display adapted to display a virtual environment to a user, a plurality of sensors coupled to the user, and a computing node including a computer readable storage medium having program instructions embodied therewith. The program instructions are executable by a processor of the computing node to cause the processor to perform a method including providing a virtual environment to a user via a virtual or augmented reality system. The method further includes presenting a sensory stimulus to the user within the virtual environment. The method further includes determining a plurality of motion parameters corresponding to a user reaction to the stimulus. The method further includes determining a user reaction time from the plurality of motion parameters by applying a time window selection model.

DETAILED DESCRIPTION

Figure 1:
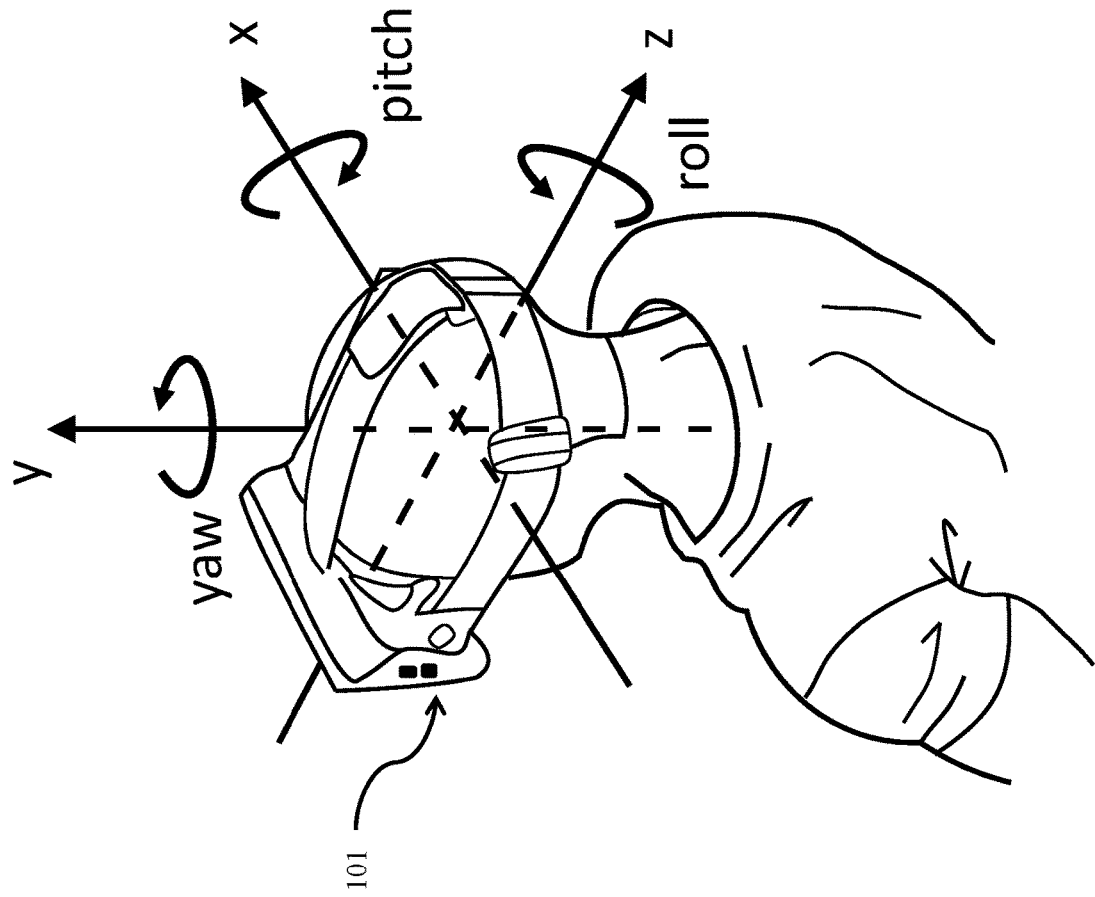
FIG. 1 illustrates an exemplary virtual reality headset according to embodiments of the present disclosure.

In physical medicine and rehabilitation, also called physical therapy, patients work with a physical therapist to enhance and/or restore their functional ability (and quality of life) after suffering physical impairment or disability. During rehabilitation therapy, patients may perform a number of exercises focused on rehabilitating a particular injured area of the body (e.g., the neck and/or limbs after a spinal injury) or part of the body that has undergone a surgical procedure (e.g., carpal tunnel surgery, knee replacement surgery, shoulder replacement surgery, hip replacement surgery, muscle/ligament repair, spinal fusion, etc.).

Current processes for rehabilitation lack objective quantified indices that reflect patient performance and enable tracking of rehabilitation progression over time, particularly for reaction time of patients who have suffered, e.g., musculoskeletal and/or neurological injury/disease. Moreover, current processes for rehabilitation lack the ability to provide detailed clinical information about the patient's condition in comparison to a control (e.g., a healthy individual or group of healthy individuals) or to another patient or group of patients with the same pathology.

Reaction time is the estimated time between the presentation of a sensory stimulus and the response to that same stimulus afterwards. Assessing and measuring reaction time can currently be performed using several different techniques including: (1) manual reaction time measurement, (2) camera-based computerized reaction time measurement, and (3) other computerized testing. For example, to assess reaction time in patients who suffered a concussion (i.e., a neurological injury), a healthcare professional may vertically suspend a ruler, allowing a portion of the ruler to rest inside the open hand of the patient. The patient is instructed to close their hand when the examiner drops the ruler, thereby catching the ruler as quickly as possible. The distance the ruler falls is recorded and converted into a reaction time using a mathematical formula for a body falling under the influence of gravity. The longer the patient's reaction time, the further up the ruler the patient will grab, if at all.

In computerized reaction time measurement, expensive laboratory equipment (e.g., optical motion capture cameras) is generally required to determine reaction time. These expensive cameras may not be found in traditional treatment/rehabilitation facilities, and thus the facility may not be capable of performing the reaction time test. Additionally, these computerized methods are generally inferior to the manual methods. Thus, these computerized methods may not provide accurate clinical information.

Various studies have been published which describe advantages and/or disadvantages of certain methods for recording response time. One exemplary published study, which is incorporated herein by reference in its entirety, describes clinical reaction time measurements and computerized reaction measurements: Eckner, J. et al. "Pilot Evaluation of a Novel Clinical Test of Reaction Time in National Collegiate Athletic Association Division 1 Football Players." *Journal of Athletic Training.* 2010. 45(4):327-332. Another exemplary published study, which is incorporated herein by reference in its entirety, describes clinical reaction time measurements and computerized reaction measurements: Eckner, J. et al. "Effect of Concussion on Clinically Measured Reaction Time in 9 NCAA Division 1 Collegiate Athletes: A Preliminary Study." *American Academy of Physical Medicine and Rehabilitation.* March 2011. Vol. 3:212-218.

Other computerized tests to measure reaction time rely on, e.g., a computer screen and a mouse click. In these computer screen-based tests, for example, the patient is asked to click the mouse when presented a stimulus to determine reaction time. These computerized methods have little to no control over the patient environment (e.g., the patient might be momentarily distracted or not looking at the screen at all). Additionally, these computerized screen tests do not imitate a functional day to day activity that reflects an everyday reaction time.

Accordingly, a need exists for a system and method that accurately assesses and measures the reaction time of a patient in response to a stimulus and enables a healthcare professional to follow the rehabilitation progression of a patient over time.

Because current implementations of response time tests generally rely on a computer based test with a mouse and a screen that changes colors for you to react upon, a more comprehensive test is needed. The VR/AR technology according to various embodiments monitors all stimulus of the user including, e.g., visual and/or voice stimulus. Moreover, the VR/AR technology according to various embodiments may determine when and where the user is looking and for how long. In various embodiments, the VR/AR technology according to various embodiments calculates the actual response time of a user to a physical stimulus in a functional environment. Additionally, the VR/AR technology according to various embodiments measures reaction time in various cognitive tasks: attention, choice reaction, task switching, and/or inhibition.

The VR/AR technology according to various embodiments provides a fully immersive environment that enables assessment and measurement of reaction time of a patient/user in response to a stimulus. In some embodiments, the VR/AR technology may allow assessment and measurement of the reaction time of the head/neck, the upper extremities (e.g., one or both arms), and/or the lower extremities (e.g., one or both legs). In various embodiments, one or more sensors may be placed on the user's body for which a reaction time is to be determined. Within this VR/AR environment, a stimulus is provided to the patient/user within the AR/VR environment. In some embodiments, the stimulus may be a virtual object presented to the user in the virtual space. In some embodiments, the user may be instructed to touch or otherwise make a motion towards the object.

Because VR/AR technology can provide detailed data about position and motion for a patient/user performing a specific reaction time test via various sensors in a head-mounted display and/or at other body parts, a VR/AR system may provide a broad understanding of patient behavior during the test to a healthcare professional. In various embodiments, data recorded by the VR/AR system may include positional and/or motion data for a head mounted display, positional and/or motion data for one or more handheld sensors, positional and/or motion data for a torso sensor, and positional and/or motion data for one or more foot-mounted sensors or leg mounted sensors. In various embodiments, data recorded by the VR/AR system may include what was in the field of view of the subject, whether the patient began an action, whether the patient stopped before completing the action, etc. In various embodiments, data from these sensors is collected at a rate of up to about 150 Hz. In various embodiments, data may be collected in six degrees of freedom: X axis translation—left/right; Y axis translation up/down/height; Z axis translation—forward/backward; P—pitch; R—roll; Y—yaw. Pitch/Roll/Yaw may be calculated in Euler angles.

Additionally, the VR/AR system may include an event recorder for recording all game events data during VR/AR sessions. In various embodiments, the event recorder may be a software module within the VR/AR system. Event data may be recorded so it can be analyzed and produce meaningful insights regarding the results of the VR/AR session. Any or all of the events which occur during the VR/AR sessions may be recorded by the event recorded. In various embodiments, appearance/disappearance of object in the VR/AR environment, patient-environment interaction, etc. are stored by the event recorder. In various embodiments, each event may contain pre-defined data related to: (1) collected sensor data in six degrees of freedom described above and (2) Unity/Unreal engine calls that are related to the VR/AR game and scenes.

To initiate a rehabilitation session with a patient/user, the VR/AR technology may instruct the patient/user to, upon receiving a sensory stimulus, react with a predetermined action. In various embodiments, the predetermined action may be, for example, a motion in the direction of the sensory stimulus or to touch/grasp an object in the VR/AR environment. In various embodiments, the VR/AR technology may present a sensory stimulus to the patient/user and begin a timer until an event is logged. In various embodiments, the event may be the predetermined action. In various embodiments, the time from the sensory stimulus until the predetermined action is logged may correspond to a patient/user reaction time.

In various embodiments, data from the event recorder may be combined with the raw positional/motion data collected from the VR/AR sensor(s). In various embodiments, the combined data may allow for simulation of the VR environment for a given patient with all relevant stimuli. In various embodiments, machine learning and/or other data analysis may be performed on the combined data to provide insights into human performance. For example, an average reaction time may be computed for a specific age bracket and/or medical condition. In another example, any suitable machine learning method as is known in the art may be implemented to predict a reaction time given a specific age bracket and/or medical condition.

In order to analyze the data recorded by the VR/AR system from the sensor(s), features are extracted. In various embodiments, relevant features may include: (1) Distance—The Euclidean distance between the relevant body part to the required stimulus location; (2) Velocity—The relevant body part's velocity; (3) Directional velocity—The relevant body part's velocity towards the stimulus (Doppler); (4) Acceleration—The relevant body part's acceleration; and (5) Directional acceleration—The relevant body part's acceleration towards the stimulus (Doppler derivative).

In various embodiments, manual labeling of reaction time may be performed for a relevant body part, such as, for example, the neck, an upper extremity, and/or a lower extremity. In combination with extracted features, manual labels may be used to train a model to predict reaction time from the extracted features.

In various embodiments, a machine learning model may be trained using the manually labeled data to predict a particular patient's reaction time in various VR/AR games and scenes. In various embodiments, the machine learning model may employ ridge regression. In various embodiments, the machine learning model may contain two parts, where each part solves for the predicted reaction time. In various embodiments, the machine learning model may receive the extracted features described above and output a predicted reaction time timestamp for a particular patient.

In various embodiments, ridge regression may be conceptualized by posing a constraint $\Sigma \beta_i^2 = c$ to the least squares problem, such that:

$$\min_{\beta}(y - X\beta)^T(y - X\beta) + \lambda(\beta^T\beta - c)$$

where $\lambda$ is the Lagrange multiplier of the constraint. The minimizer of the problem is the simple ridge estimator:

$$\hat{\beta}_R = (X^TX + \lambda I)^{-1} X^T y$$

where I is the identity matrix and the ridge parameter $\lambda$ serves as the positive constant shifting the diagonals, thereby decreasing the condition number of the moment matrix. In a linear regression-type model, a ridge regression line may be expressed as a minimization of the sum of the squared residuals in addition to a ridge regression penalty, which is A multiplied by the slope squared.

In various embodiments, the ridge-regression model may focus on optimizing the model hyper-parameter (alpha), which corresponds to model accuracy. In various embodiments, cross-validation may be employed to train the model while providing for the generalizability of the results to an independent data set. In various embodiments, cross-validation may include repeatedly splitting the data into a training set and a validation set, training the model using the respective training set, and testing the accuracy of the model using the respective validation set. As set out below, in various embodiments, an outer model trains an inner model.

In various embodiments, the machine learning model includes two sub-models, one determining time window selection, and one determining time window shrinkage, as described below. In some embodiments, both models utilize ridge regression as described above, and include an inner and an outer model.

In various embodiments, any of the machine learning models described herein may be any suitable regression analysis model as is known in the art (e.g., a generalized linear model). More generally, it will be appreciated that a variety of machine learning techniques are suitable for estimating and predicting the relationship between input features and a dependent variable. In various embodiments, the sub-models may utilize the same or different machine learning models. For example, the time window selection may use a ridge regression model while the time window shrinkage model may utilize a generalized linear model. In various embodiments, one or both sub-models may use the same machine learning model for the inner and outer models (e.g., the outer model and the inner model both use ridge regression). In various embodiments, one or both sub-models may use different machine learning models for the inner and outer models (e.g., the outer model uses ridge regression and the inner model uses a generalized linear model, or vice versa). In various embodiments, some machine learning models may be more appropriate (e.g., provide better results) than other machine learning models for the outer model (i.e., providing a rough estimate). In various embodiments, some machine learning models may be more appropriate (e.g., provide better results) than other machine learning models for the inner model (i.e., refining the rough estimate).

In various embodiments, the time window selection sub-model selects a set of upper and lower time boundaries having a fixed delta therebetween such that the reaction time timestamp located in the center of the two boundaries. The inner model predicts, for each window, where the window is located relative to the reaction time timestamp. The inner model of the time window selection sub-model produces a score for each possible window, addresses a window that holds the correct reaction time timestamp in its center, and outputs the highest score achieved (the most accurate window compared to the true reaction time timestamp). The outer model finds the window that holds the response time in its center. In various embodiments, the outer model averages all scores per alpha and selects the alpha with the highest score. Thus, the outer model predicts the correct time window having the response time timestamp. In various embodiments, the outer model trains the inner model according to the minimal error of the outer model.

In various embodiments, a time window shrinkage sub-model compresses the window's size (from one or both sides) to a single, smaller timestamp window.

An inner model predicts, for each window, where the respective window is relative to the response time (similar to the time window selection inner model, but using a different window size). In various embodiments, the inner model indicates which end of the window is optimal for shrinking by comparing the two options (i.e., lower and upper boundaries).

The outer model finds the correct end of the window to cut in order to keep the reaction time in the window's center. In various embodiments, the outer model averages all scores per alpha and selects the alpha with the highest score. Thus, the outer model may predict the correct end of the window from which to cut. The outer model trains the inner model according to the minimal error of the outer model.

In various embodiments, the outer model is repeatedly applied in a loop for each shrinking step until the window size is minimal.

In various embodiments, the time window selection sub-model and the time window shrinkage sub-model are applied together to the input data, each set of features being input into each sub-model to output a specific reaction time timestamp. Each set of features may be sequentially input into the time window selection sub-model and then into the time window shrinkage sub-model.

In various embodiments, any of the machine learning models described above may be a part of a learning system.

In some embodiments, a feature vector, including features such as those described above, is provided to the learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

It will be appreciated that a variety of virtual and augmented reality devices are known in the art. For example, various head-mounted displays providing either immersive video or video overlays are provided by various vendors. Some such devices integrate a smart phone within a headset, the smart phone providing computing and wireless communication resources for each virtual or augmented reality application. Some such devices connect via wired or wireless connection to an external computing node such as a personal computer. Yet other devices may include an integrated computing node, providing some or all of the computing and connectivity required for a given application.

Virtual or augmented reality displays may be coupled with a variety of motion sensors in order to track a user's motion within a virtual environment. Such motion tracking may be used to navigate within a virtual environment, to manipulate a user's avatar in the virtual environment, or to interact with other objects in the virtual environment. In some devices that integrate a smartphone, head tracking may be provided by sensors integrated in the smartphone, such as an orientation sensor, gyroscope, accelerometer, or geomagnetic field sensor. Sensors may be integrated in a headset, or may be held by a user, or attached to various body parts to provide detailed information on user positioning.

In various embodiments, a user is furnished with a VR or AR system. As noted above, a VR or AR system will generally have integrated motion sensors. In addition, additional motions sensors may be provided, for example to be handheld. This allows tracking of multiple patient attributes while they interact with a scene. In this way, systematic and reproducible scenarios may be used to assess the subject's function.

With reference now to FIG. 1, an exemplary virtual reality headset is illustrated according to embodiments of the present disclosure. In various embodiments, system 100 is used to collected data from motion sensors including hand sensors (not pictured), sensors included in headset 101, and additional sensors such as sensors placed on the body (e.g., torso, limbs, etc.) or a stereo camera. In some embodiments, data from these sensors is collected at a rate of up to about 150 Hz. As illustrated, data may be collected in six degrees of freedom: X axis translation—left/right; Y axis translation—up/down/height; Z axis translation forward/backward; P—pitch; R—roll; Y—yaw. As set out herein, this data may be used to track a user's overall motion to facilitate interaction with a virtual environment and to evaluate their performance. Pitch/Roll/Yaw may be calculated in Euler angles.

Figure 2:
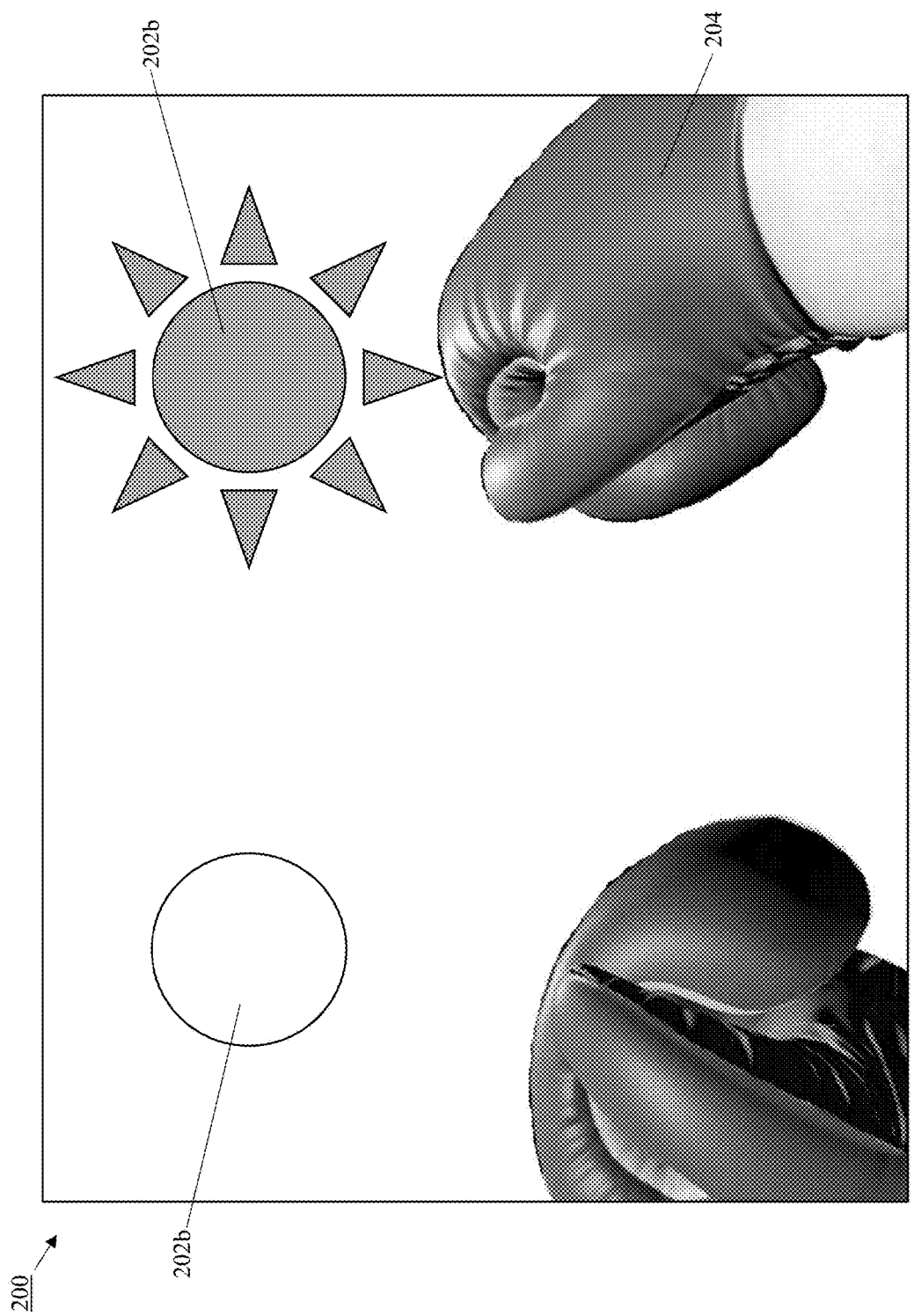
FIG. 2 illustrates an exemplary VR/AR environment with a sensory stimulus for determining a reaction time of a patient/user according to embodiments of the present disclosure.

FIG. 2 illustrates an exemplary VR/AR environment 200 with a sensory stimulus for determining a reaction time of a patient/user according to embodiments of the present disclosure. As shown in FIG. 2, the VR/AR environment 200 includes virtual objects 202a, 202b (e.g., lights) that provide a sensory stimulus to the user for the determination of reaction time. In FIG. 2, one light 202a is not lit while light 202b is lit to indicate to the user to motion towards the light 202b that is lit (e.g., punch the light). In various embodiments, both lights 202a, 202b may be lit to signal to the user to As described above, the VR/AR system 200 may predict a response time from the time one light (or both lights) is lit until the time the virtual object 202b is hit by the user. In various embodiments, the response time may be predicted based on the detection of the initiation of a movement towards the sensory stimulus (e.g., the light).

In various embodiments, the systems provided herein may record a predetermined number of reaction times to generate a training dataset to thereby train a machine learning system (e.g., neural network) to determine a window of time in which a future reaction time may occur. The predetermined number of reaction times recorded may be any suitable number of reaction times to produce a suitable dataset for training the machine learning system (e.g., 10, 100, 1,000, 10,000, 100,000, etc.). In various embodiments, the systems provided herein may train a population model, subpopulation model, and/or an individualized model. If training a subpopulation model, the subpopulation model may include groups based on one or more parameters, such as, for example, age, gender, location, etc.

Figure 3A:
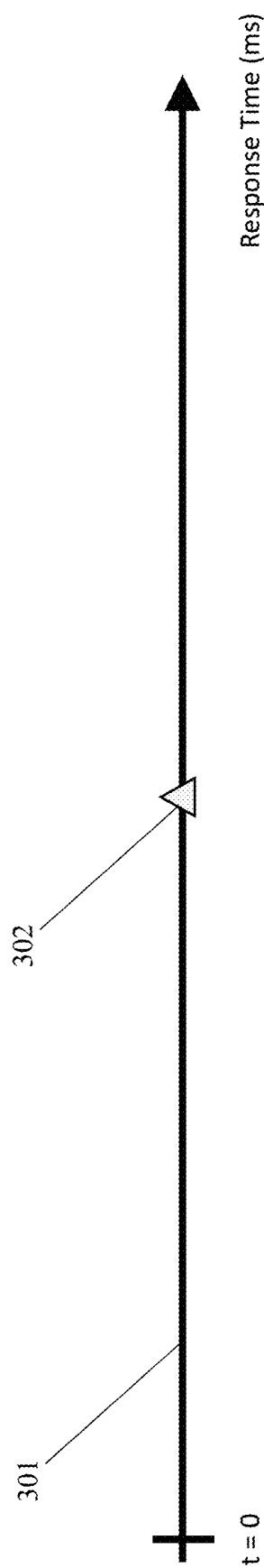
FIGS. 3A-3E illustrates an exemplary process for determining a reaction time of a patient using a time window selection model and time window shrinkage model according to embodiments of the present disclosure.

FIGS. 3A-3E illustrates an exemplary process for determining a reaction time of a patient using a time window selection model (FIGS. 3B-3C) and time window shrinkage model (FIGS. 3D-3E) according to embodiments of the present disclosure. FIG. 3A illustrates a one dimensional graph 301 of time (in milliseconds) where t equals zero represents the instance that the sensory stimuli is presented to the user and the mark 302 indicates the actual user's response time (i.e., the time taken by the user to receive the sensory stimulus and react, e.g., by punching the light) that the VR/AR system is attempting to predict. In various embodiments, the system may record various motion parameters of the user as the user reacts to the sensory stimulus. In various embodiments, the system may record the distance (e.g., Euclidean distance) of a relevant part of the user's body (e.g., a hand) travels during the reaction to the sensory stimulus location. In various embodiments, the system may record the velocity of the part of the relevant part of the user's body (e.g., hand, foot, head, etc.). In various embodiments, the system may record a directional velocity of the part of the relevant part of the user's body towards the stimulus (e.g., Doppler). In various embodiments, the system may record the acceleration of the part of the relevant part of the user's body (e.g., hand, foot, head, etc.). In various embodiments, the system may record a directional acceleration of the part of the relevant part of the user's body towards the stimulus (e.g., Doppler derivative). In various embodiments, using one or more of the above recorded motion parameters, the system may determine a time window into which future reaction times may fall via a machine learning system (e.g., neural network).

Figure 3B:
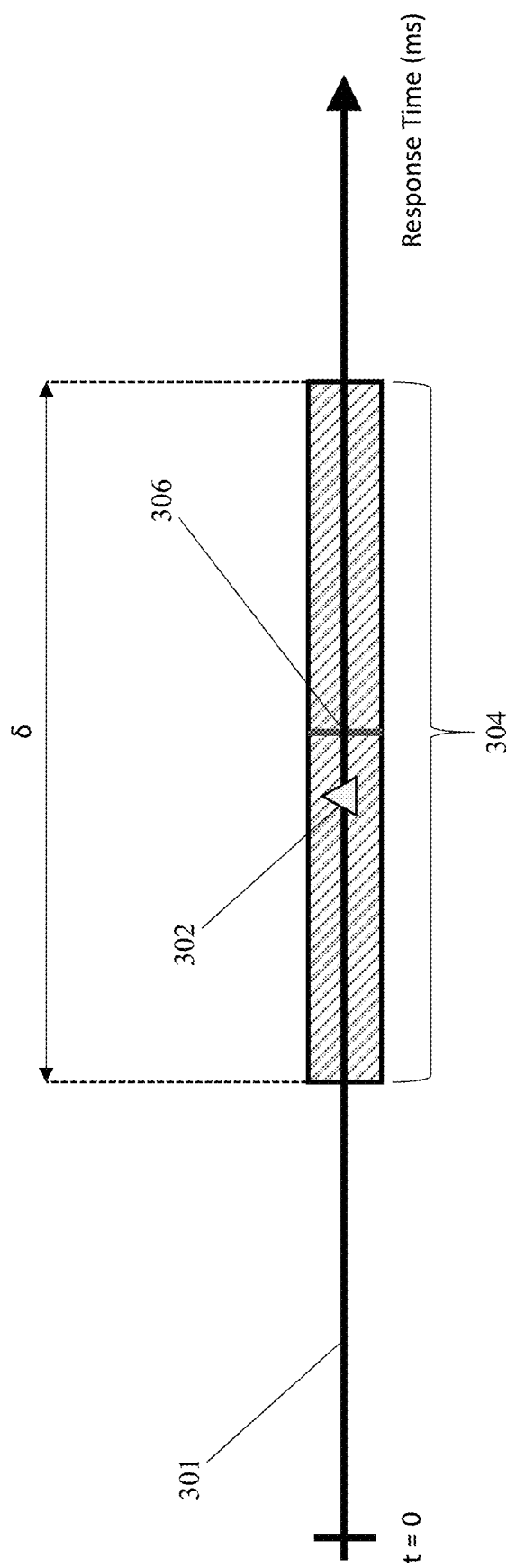

In various embodiments, the system applies a time window selection model using an outer model. As shown in FIG. 3B, the outer model provides a rough estimation of a time window that is centered at the mark 302 representing the response time. First, an upper boundary and a lower boundary for a time window 304 given a fixed delta, δ, are selected. In various embodiments, delta, δ, may be determined to provide a predetermined (e.g., the highest) accuracy of the model. In various embodiments, delta, δ, may be determined using a validation process. For example, a chosen delta may be compared against other possible values in a set of possible delta values to validate that the chosen delta provides the best accuracy in the set of delta values. In various embodiments, the outer model may average all scores per alpha and selects the ridge regression model associated with the alpha having the highest score.

In various embodiments, delta may remain constant for all patients. In various embodiments, different values for delta may be selected for each identified patient population type. In various embodiments, the response time prediction model may predict a patient reaction time independently of patient population (i.e., no patient population type is required by the prediction model to predict reaction time).

In various embodiments, a score determined for an inner model ("inner score") is computed as a distance between a current index to a real response time index, divided by the size of the window. In various embodiments, inner scores are calculated for each window. In various embodiments, a score determined for an outer model ("outer score") is computed as 1 minus an absolute distance between a current index to a real response time index, divided by half the size of the window. In various embodiments, outer scores are calculated for each user hit.

In various embodiments, each alpha represents a different machine learning model (e.g., ridge regression model) that is trained over all possible windows and fit using the inner scores. In various embodiments, each model provides a different outer score for every user hit. In various embodiments, the machine learning model (e.g., ridge regression model) that provides the highest average outer score when used for the prediction process is selected by the system.

Figure 3C:
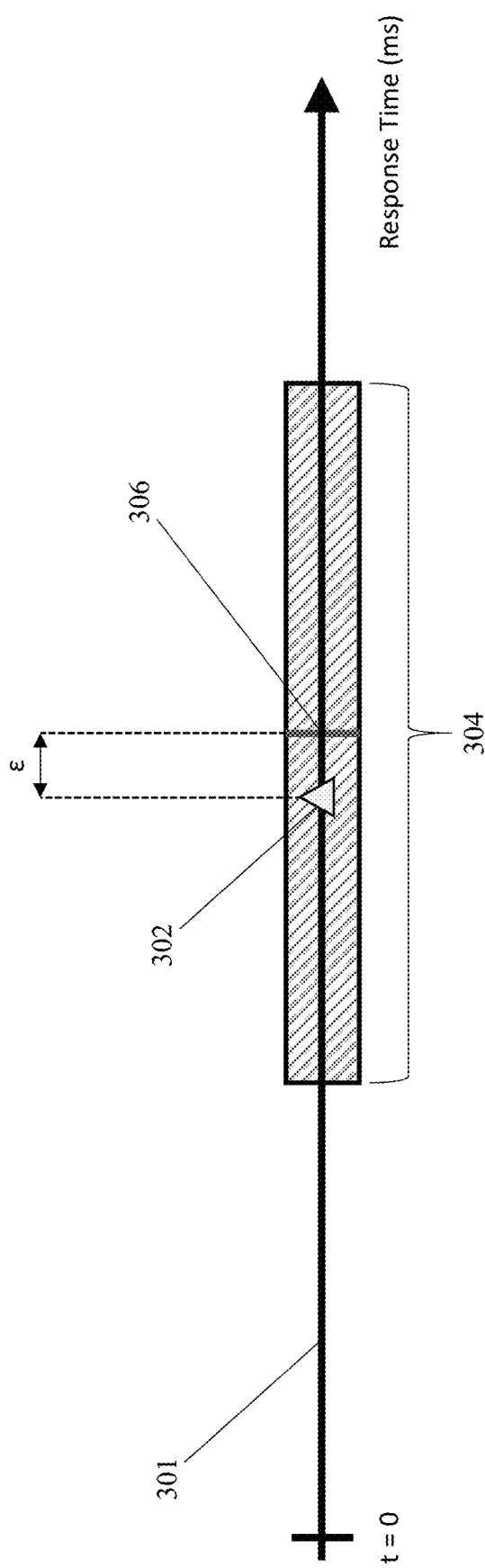

In various embodiments, the system refines the selected time window from the outer model via an inner model. In various embodiments, the inner model is trained according to the minimal error of the time window selections of the outer model. In various embodiments, the inner model determines where the center 306 of the time window is relative to the mark 302 representing the response time. As shown in FIG. 3C, the inner model determines the error, E, in the selected time window 304 defined as the difference between the center 306 of the time window 304 and the mark 302 representing the response time. In various embodiments, the inner model computes a score for each time window (e.g., of all possible time windows for each hit) and determines the maximum score out of the computed scores. As described above, in various embodiments, the inner score may be determined as a distance from a real response time to a current index.

Figure 3D:
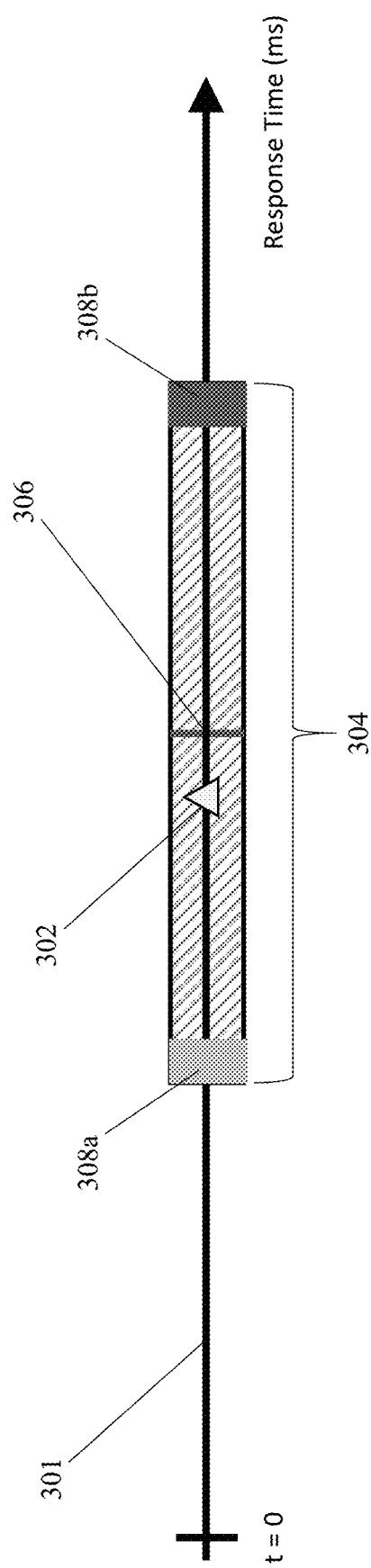

In various embodiments, the system applies a time window shrinkage model using an outer model. As shown in FIG. 3D, the outer model provides a rough estimation by determining which end 308a, 308b of the selected time window 304 to cut. In various embodiments, the outer model may provide various options of side and/or amount for shrinking the time window, where each option is selected based on a machine learning model (e.g., ridge regression model). In various embodiments, the outer model may be trained to shrink the sample that has a larger distance from the real response time. In various embodiments, the larger the distance in the outer model, the larger the penalty for choosing the other sample. In various embodiments, the outer model may average all scores per alpha and selects the ridge regression model associated with the alpha having the highest score.

Figure 3E:
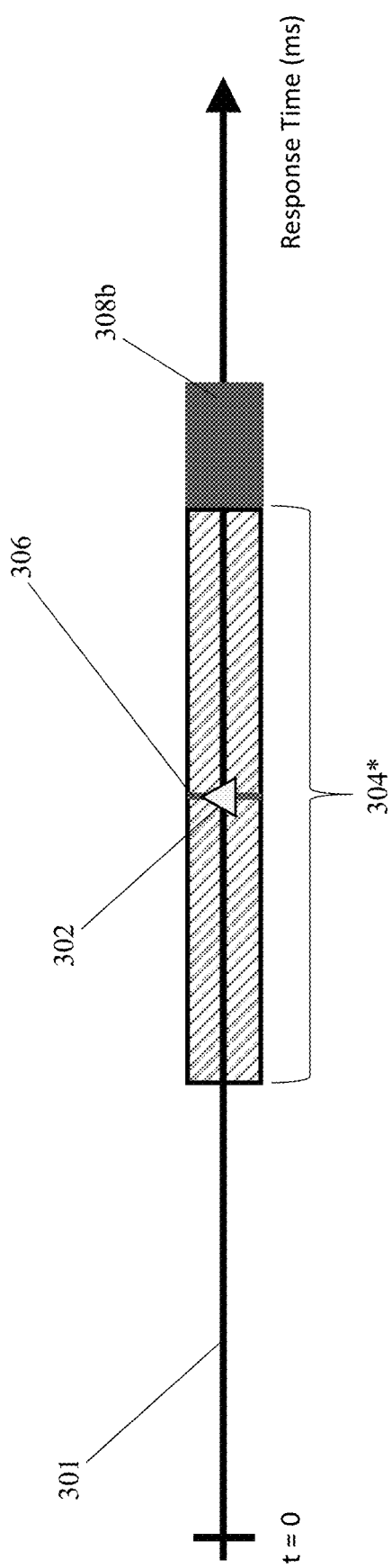

In various embodiments, the system refines the time window shrinkage from the outer model via an inner model. In various embodiments, for a given shrinkage model, the inner model may be trained to provide an accurate score for each given window. In various embodiments, the inner model provides a score for each of the shrinkage options generated by the outer model and then selects the best shrinkage option to shrink the time window such that the center of the time window 306 is at the response time 302. As shown in FIG. 3E, the original time window 304 is shrunk such that the center 306 of the shrunk time window 304* is at the mark 302 representing the response time.

It will be appreciated that, in some embodiments, an ensemble model (e.g., an ensemble of ridge regression models) is applied at the prediction phase, while in some embodiments, while an ensemble of models is generated during training, only a best performing model is applied at the prediction phase.

Figure 4A:
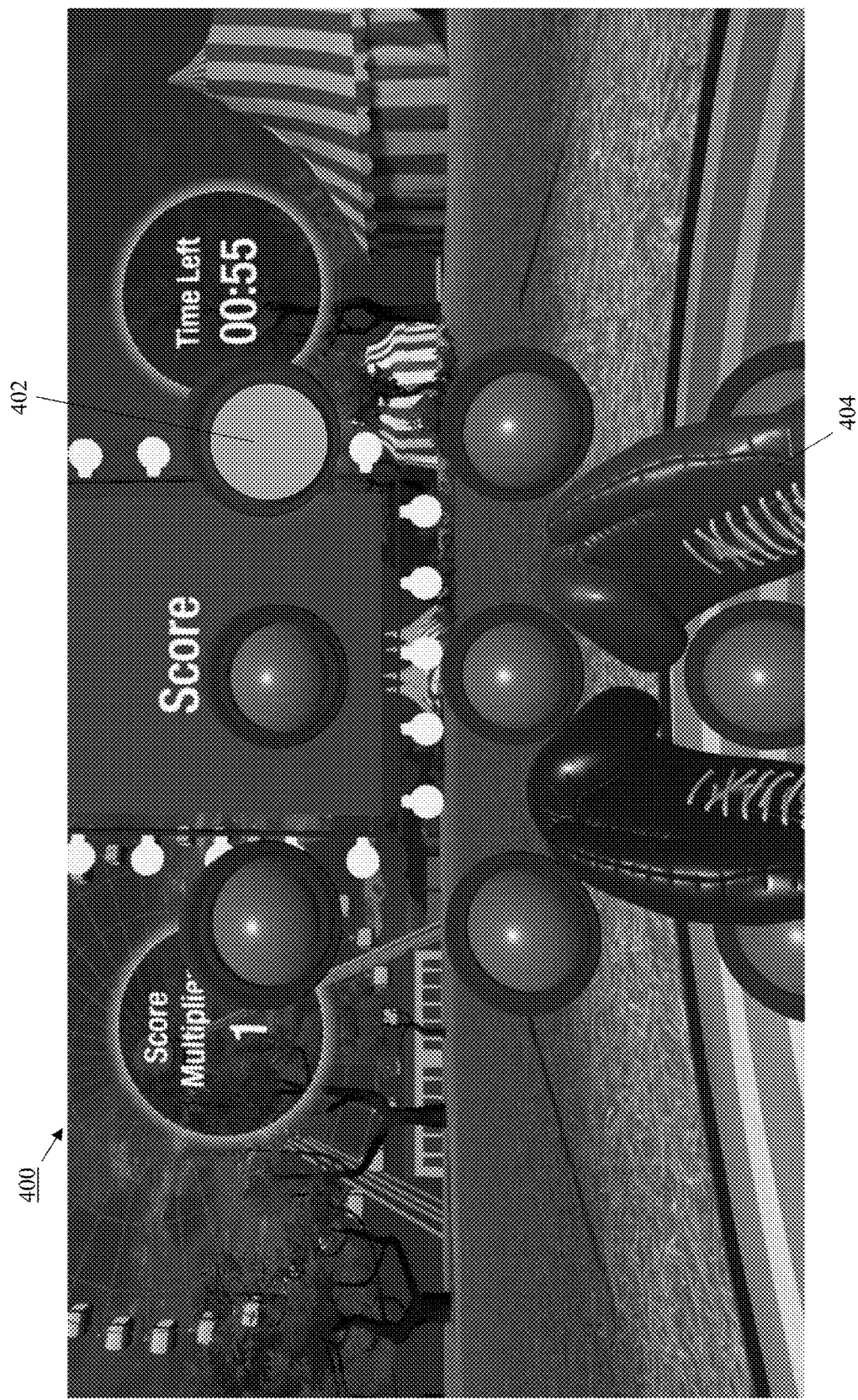
FIG. 4A illustrates an exemplary VR environment having a sensory stimulus (e.g., lightbulbs) for determining a reaction time of a patient/user.

FIG. 4A illustrates an exemplary VR environment 400 having a sensory stimulus (e.g., lightbulbs) 402 for determining the reaction time of a patient/user 404. As illustrated in FIG. 4A, the user 404 is presented with a series of nine lightbulbs arranged in a grid pattern. One skilled in the art will recognize that any suitable number of lightbulbs may be displayed in any suitable arrangement (e.g., vertical, horizontal, or diagonal line) as is known in the art The VR environment 400 may instruct the user 404 to punch towards the lightbulb 402 that is lit. In various embodiments, the lightbulb 402 may be lit with a first color (e.g., red) representing the left hand and lit with a second color (e.g., blue) representing the right hand. In various embodiments, the VR environment 400 may instruct the user 404 to punch any of the lightbulbs having the first color (e.g., red) with one hand (e.g., left) and/or to punch any of the lightbulbs having the second color (e.g., blue) with the other hand (e.g., right). In various embodiments, a response time may be measured from when the lightbulb is lit to when the user 404 successfully punches (or motions towards) the lightbulb. In various embodiments, the response time may be logged only when the user 404 punches with the correct hand corresponding to the color of the lightbulb. In various embodiments, a score may be assigned to the user 404 based on successfully punching the lightbulb 402 with the correct hand. In various embodiments, a lower score (or a score of zero) may be assigned to the user 404 for punching a lightbulb that is not lit or punching a lit lightbulb 402 with the wrong hand.

Figure 4B:
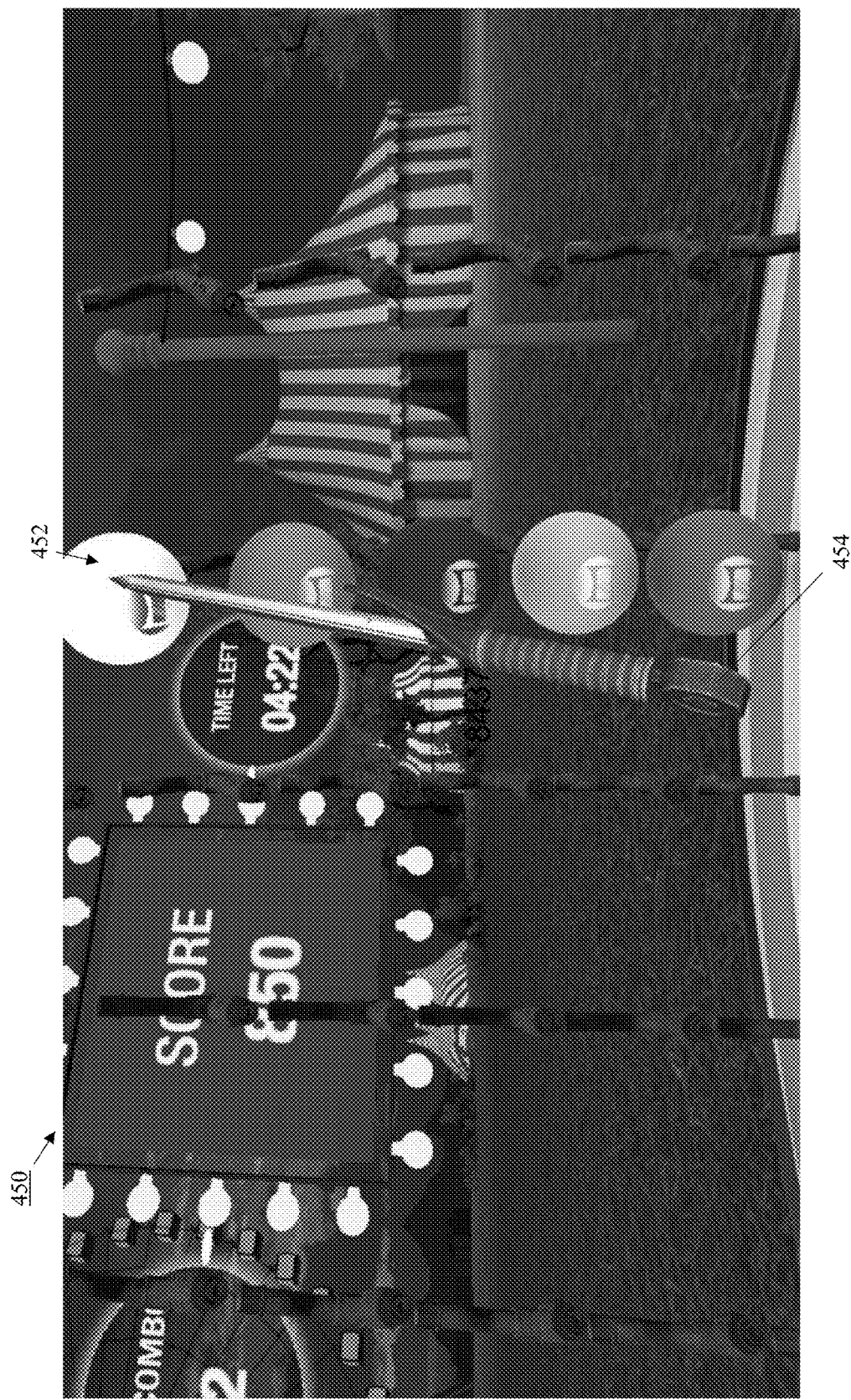
FIG. 4B illustrates an exemplary VR environment having a sensory stimulus (e.g., balloons) for determining a reaction time of a patient/user.

FIG. 4B illustrates an exemplary VR environment 450 having a sensory stimulus (e.g., balloons) 452 for determining a reaction time of a patient/user 454. As illustrated in FIG. 4B, the user 454 is presented with a series of five balloons arranged in a straight, vertical line. One skilled in the art will recognize that any suitable number of balloons may be displayed in any suitable arrangement (e.g., horizontal or diagonal line) as is known in the art. The VR environment 450 may instruct the user 454 to motion in a particular direction of the balloons arrangement (e.g., up or down) such that all balloon are popped. In various embodiments, the balloons 452 may include a first color (e.g., red) corresponding to the left hand. In various embodiments, the balloons 452 may include a second color (e.g., blue) corresponding to the right hand. In various embodiments, the VR environment 450 may instruct the user 404 to motion towards the balloons having the first color (e.g., red) with one hand (e.g., left) and/or to motion having the second color (e.g., blue) with the other hand (e.g., right). In various embodiments, a response time may be measured from when the user 454 is provided instruction to when the user 454 pops all balloons 452 in the arrangement. In various embodiments, the response time may be logged only when the user 454 motions with the correct hand corresponding to the color of the balloons 452. In various embodiments, a score may be assigned to the user 404 based on successfully popping the balloons 452 with the correct hand. In various embodiments, a lower score (or a score of zero) may be assigned to the user 454 for popping one or more balloons 452 with the wrong hand or missing balloons 452 in the arrangement.

Figure 5:
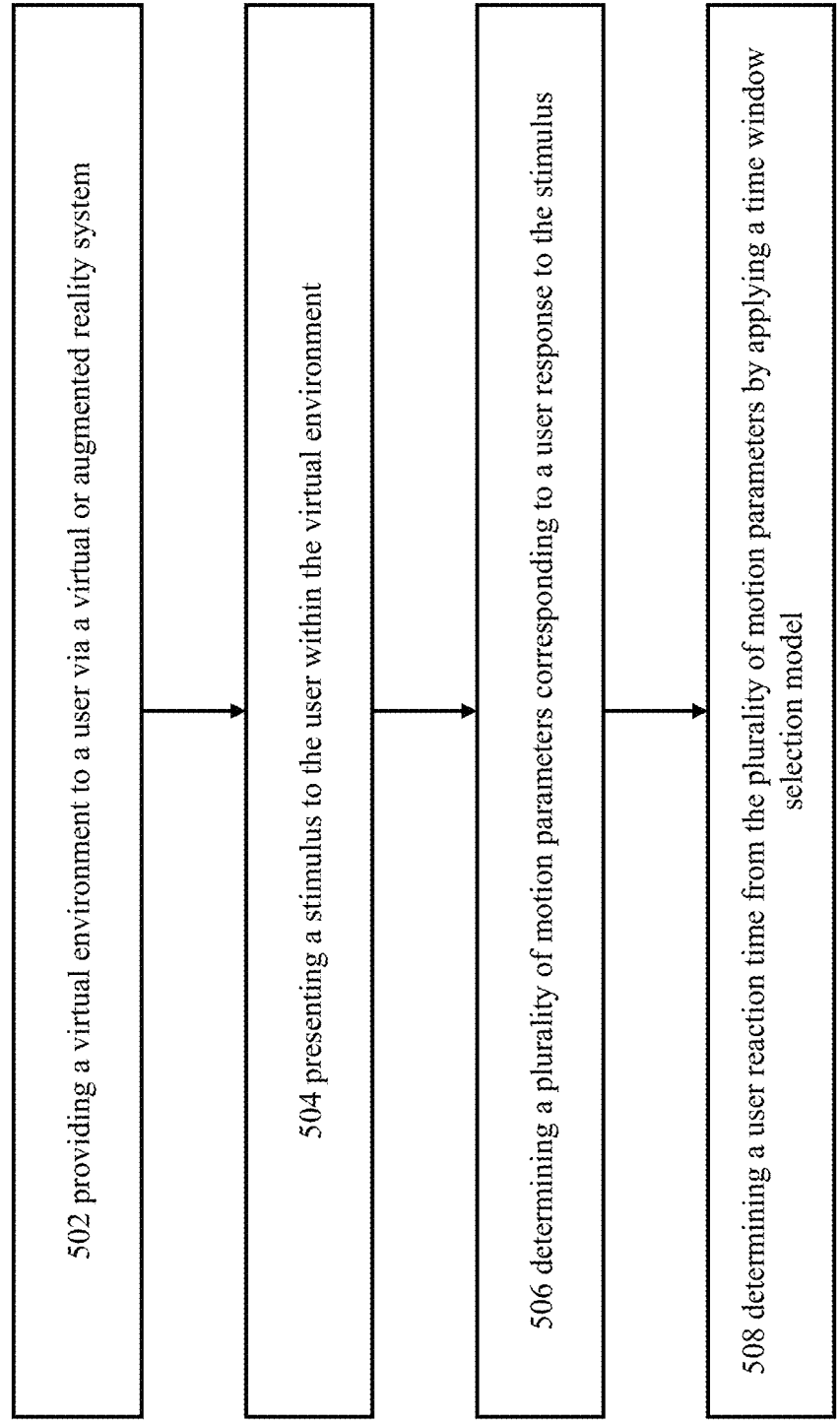
FIG. 5 is a flow chart illustrating an exemplary method for determining a reaction time from a patient/user in a VR/AR environment.

FIG. 5 illustrates a flowchart for a method for guiding a patient/user through an exercise and providing real time feedback to the patient/user. At 502, the method includes providing a virtual environment to a user via a virtual or augmented reality system. At 504, the method includes presenting a sensory stimulus to the user within the virtual environment. At 506, the method includes determining a plurality of motion parameters corresponding to a user response to the stimulus. At 508, the method includes determining a user reaction time from the plurality of motion parameters by applying a time window selection model. In various embodiments, determining the user reaction time further includes applying a time window shrinkage model. In various embodiments, the time window selection model and/or the time window shrinkage model may include an outer model and an inner model. In various embodiments, the inner model is trained on the outer model.

In various embodiments, off the shelf VR systems are optionally used with additional external compatible sensors to track various elements in multiple fields including, e.g., motion tracking, cognitive challenges, speech recognition, stability, facial expression recognition, and biofeedback.

Motion tracking can include, but is not limited to tracking of gait, stability, tremors, amplitude of motion, speed of motion, range of motion, and movement analysis (smoothness, rigidity, etc.).

Cognitive challenges can include, but is not limited to reaction time, success rate in cognitive challenges, task fulfillment according to different kind of guidance (verbal, written, illustrated, etc.), understanding instructions, memory challenges, social interaction, and problem solving.

Speech Recognition can include, but is not limited to fluent speech, ability to imitate, and pronunciation.

Stability can include, but is not limited to postural sway.

Bio-Feedback can include, but is not limited to, Heart rate variability (HRV), Electrothermal activity (EDA), Galvanic skin response (GSR), Electroencephalography (EEG), Electromyography (EMG), Eye tracking, Electrooculography (EOG), Patient's range of motion (ROM), Patient's velocity performance, Patient's acceleration performance, and Patient's smoothness performance.

Figure 6:
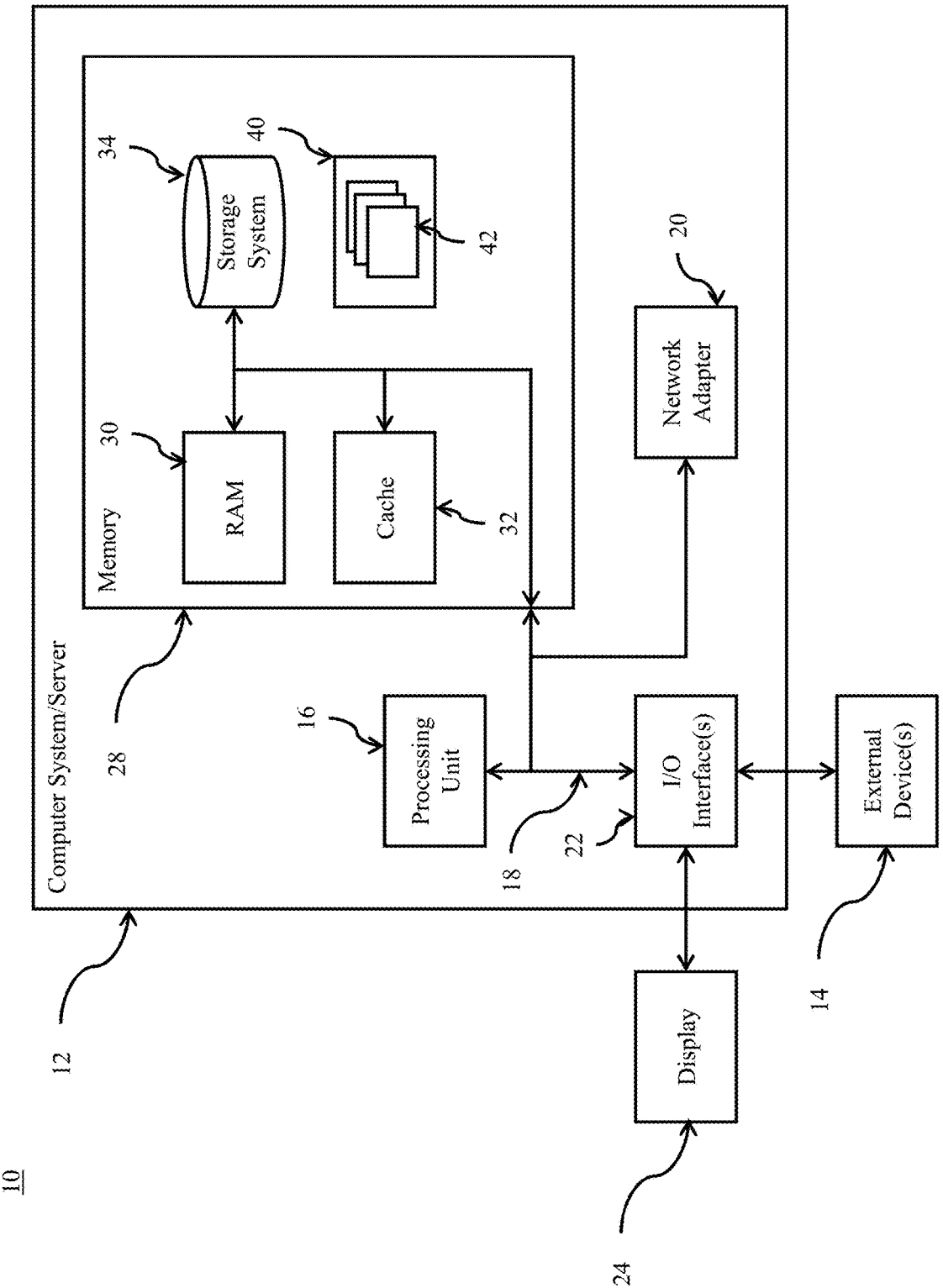
FIG. 6 depicts an exemplary computing node according to embodiments of the present disclosure.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   providing a virtual environment to a user via a virtual or augmented reality system;
   presenting a sensory stimulus to the user within the virtual environment;
   determining a plurality of motion parameters corresponding to a user response to the stimulus; and
   determining a user reaction time from the plurality of motion parameters by:
      applying a time window selection model to determine a plurality of time windows, each having a predetermined width and a center;
      selecting a first time window from the plurality of time windows based on a recorded reaction time of the user and the center of each of the plurality of time windows;
      applying a time window shrinkage model to determine a shrinkage to the predetermined width of the selected time window;
      shrinking the selected time window based on the shrinkage to generate a plurality of new time windows with a reduced width.

2. The method of claim 1, wherein the time window selection model comprises a ridge regression model.

3. The method of claim 2, wherein the time window selection model comprises a first outer model and a first inner model.

4. The method of claim 3, wherein the first inner model is trained by the first outer model.

5. The method of claim 4, wherein the first inner model determines an error between the recorded reaction time and the center of each of the plurality of time windows.

6. The method of claim 5, wherein the time window shrinkage model comprises a ridge regression model.

7. The method of claim 6, wherein the time window shrinkage model comprises a second outer model and a second inner model.

8. The method of claim 7, wherein the second inner model is trained by the second outer model.

9. The method of claim 8, wherein the second outer model determines an end of the time window to cut.

10. The method of claim 9, wherein the second inner model determines an amount of the window to cut such that the center of the time window is equal to the reaction time.

11. The method of claim 1, wherein the plurality of motion parameters comprises distance, velocity, directional velocity, acceleration, and directional acceleration.

12. The method of claim 1, wherein the user response is an initiation of movement towards the stimulus.

13. The method of claim 1, wherein determining the user reaction time comprises determining a recorded reaction time of a body part comprising a neck, an upper extremity, and a lower extremity.

14. The method of claim 1, wherein the virtual environment comprises at least one virtual object configured to provide the sensory stimulus to the user.

15. The method of claim 14, wherein the sensory stimulus is a visual stimulus.

16. A system comprising:
   a virtual or augmented reality display adapted to display a virtual environment to a user;
   a plurality of sensors coupled to the user;
   a computing node comprising a computer readable storage medium having program instructions embodied therewith, the program instructions executable by a processor of the computing node to cause the processor to perform a method comprising:
      providing the virtual environment to the user via the virtual or augmented reality display;
      presenting a sensory stimulus to the user within the virtual environment;
      determining a plurality of motion parameters corresponding to a user response to the stimulus; and
      determining a user reaction time from the plurality of motion parameters by:
         applying a time window selection model to determine a plurality of time windows, each having a predetermined width and a center;
         selecting a first time window from the plurality of time windows based on a recorded reaction time of the user and the center of each of the plurality of time windows;
         applying a time window shrinkage model to determine a shrinkage to the predetermined width of the selected time window;
         shrinking the selected time window based on the shrinkage to generate a plurality of new time windows with a reduced width.

17. The system of claim 16, wherein the time window selection model comprises a ridge regression model.

18. The system of claim 17, wherein the time window selection model comprises a first outer model and a first inner model.

19. The system of claim 18, wherein the first inner model is trained by the first outer model.

20. The system of claim 18, wherein the first inner model determines an error between the recorded reaction time and the center of each of the plurality of time windows.

21. The system of claim 20, wherein the time window shrinkage model comprises a ridge regression model.

22. The system of claim 21, wherein the time window shrinkage model comprises a second outer model and a second inner model.

23. The system of claim 22, wherein the second inner model is trained by the second outer model.

24. The system of claim 23, wherein the second outer model determines an end of the time window to cut.

25. The system of claim 24, wherein the second inner model determines an amount of the window to cut such that the center of the time window is equal to the reaction time.

26. The system of claim 16, wherein the plurality of motion parameters comprises distance, velocity, directional velocity, acceleration, and directional acceleration.

27. The system of claim 16, wherein the user response is an initiation of movement towards the stimulus.

28. The system of claim 16, wherein determining the user reaction time comprises determining a recorded reaction time of a body part comprising a neck, an upper extremity, and a lower extremity.

29. The system of claim 16, wherein the virtual environment comprises at least one virtual object configured to provide the sensory stimulus to the user.

30. The system of claim 29, wherein the sensory stimulus is a visual stimulus.

31. A computer program product comprising a computer readable storage medium having program instructions embodied therewith, the program instructions executable by a processor to cause the processor to perform a method comprising:
   providing a virtual environment to a user via a virtual or augmented reality system;
   presenting a sensory stimulus to the user within the virtual environment;
   determining a plurality of motion parameters corresponding to a user response to the stimulus; and
   determining a user reaction time from the plurality of motion parameters by:
      applying a time window selection model to determine a plurality of time windows, each having a predetermined width and a center;
      selecting a first time window from the plurality of time windows based on a recorded reaction time of the user and the center of each of the plurality of time windows;
      applying a time window shrinkage model to determine a shrinkage to the predetermined width of the selected time window;
      shrinking the selected time window based on the shrinkage to generate a plurality of new time windows with a reduced width.

32. The computer program product of claim 31, wherein the time window selection model comprises a ridge regression model.

33. The computer program product of claim 32, wherein the time window selection model comprises a first outer model and a first inner model.

34. The computer program product of claim 33, wherein the first inner model is trained by the first outer model.

35. The computer program product of claim 33, wherein the first inner model determines an error between the recorded reaction time and the center of each of the plurality of time windows.

36. The computer program product of claim 35, wherein the time window shrinkage model comprises a ridge regression model.

37. The computer program product of claim 36, wherein the time window shrinkage model comprises a second outer model and a second inner model.

38. The computer program product of claim 37, wherein the second inner model is trained by the second outer model.

39. The computer program product of claim 38, wherein the second outer model determines an end of the time window to cut.

40. The computer program product of claim 39, wherein the second inner model determines an amount of the window to cut such that the center of the time window is equal to the reaction time.

41. The computer program product of claim 31, wherein the plurality of motion parameters comprises distance, velocity, directional velocity, acceleration, and directional acceleration.

42. The computer program product of claim 31, wherein the user response is an initiation of movement towards the stimulus.

43. The computer program product of claim 31, wherein determining the user reaction time comprises determining a recorded reaction time of a body part comprising a neck, an upper extremity, and a lower extremity.

44. The computer program product of claim 31, wherein the virtual environment comprises at least one virtual object configured to provide the sensory stimulus to the user.

45. The computer program product of claim 44, wherein the sensory stimulus is a visual stimulus.

46. The method of claim 1, further comprising: reapplying the time window selection model with the reduced width until the reduced width is below a certain threshold.

47. The system of claim 16, wherein the method further comprises: reapplying the time window selection model with the reduced width until the reduced width is below a certain threshold.

48. The computer program product of claim 31, wherein the method further comprises: reapplying the time window selection model with the reduced width until the reduced width is below a certain threshold.

* * * * *